Jan. 5, 1971 D. W. ULERY Plant Pat. 3,012

BEGONIA PLANT

Filed April 23, 1969

INVENTOR
DALE W. ULERY
BY Rummler & Snow
Attys

United States Patent Office

Plant Pat. 3,012
Patented Jan. 5, 1971

3,012
BEGONIA PLANT

Dale W. Ulery, Springfield, Ohio, assignor to Ulery Greenhouse Company, Springfield, Ohio, a corporation of Ohio Filed Apr. 23, 1969, Ser. No. 818,849
Int. Cl. A01h 5/00
U.S. Cl. Plt.—68 1 Claim

ABSTRACT OF THE DISCLOSURE

A new variety of *semperflorens* begonia plant having very large red blooms and extremely vigorus and husky growth qualities, the new plant originating as a sport of Swansson Double Rose (unpatented).

BACKGROUND OF THE INVENTION

My new variety of begonia plant was discovered by me as a sport of a Swansson Double Rose begonia plant being cultivated by me in greenhouse facilities at Springfield, Ohio, and is the result of asexual propagation of the said sport by means of cuttings. This new variety was observed to have extraordinarily large flowers of a bright, distinctive red color and a husky, vigorous growth habit far surpassing the corresponding characteristics of the known commercial begonia varieties. For these reasons, asexual propagation of this new variety, by cuttings from stock plants, has been carried through many generations, with the object of ultimate commercial exploitation, and all descendants of the original discovery have consistently exhibited the same extraordinary characteristics found in the original plant. Such propagation is now being done at Springfield, Ohio, and the distinctive features of the new variety have proved to be fixed and to hold true.

DESCRIPTION OF THE DRAWING

The new variety of begonia plant is illustrated in the accompanying photographic drawings in which.

DESCRIPTION OF THE NEW PLANT

Figure 2:
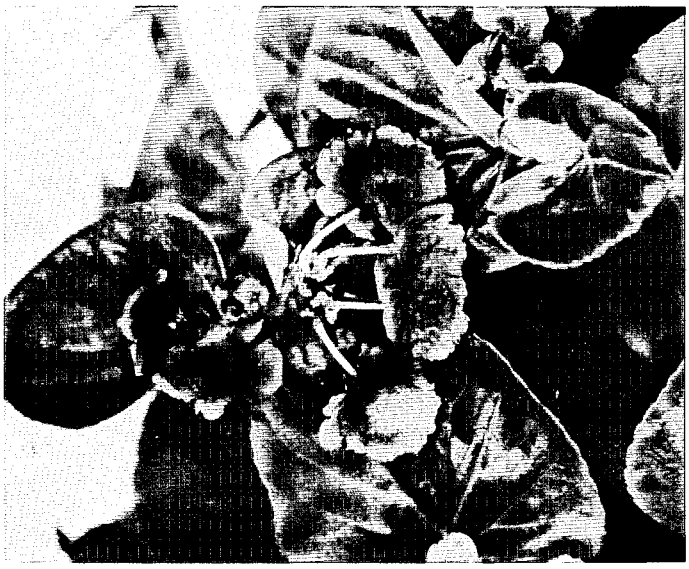
FIG. 2 is a close-up, more detailed view, showing the foliage and the manner of display of the blooms.
Figure 1:
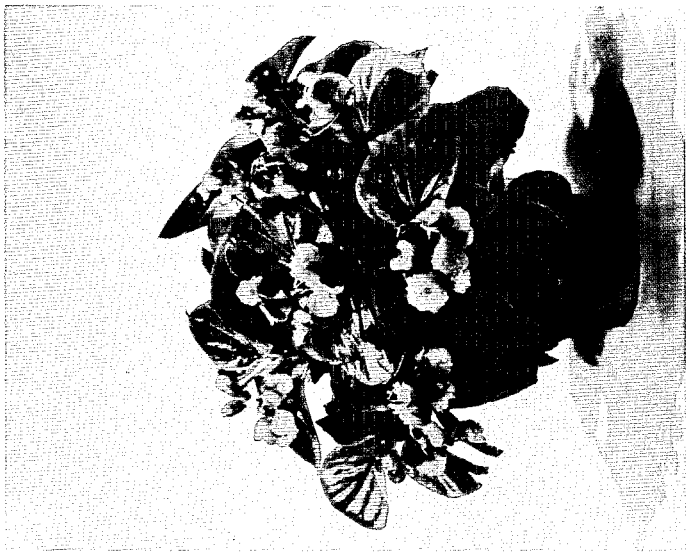
FIG. 1 shows the general form of the plant and its foliage.

The following is a detailed description of my new variety of begonia plant with color designations according to "A Dictionary of Color" by Maerz & Paul.

THE PLANT

Origin: Sport of Swansson Double Rose (unpatented).
Botanic name: *Begonia semperflorens flore-plena.*
Commercial name: Double Wax Begonia.
Form: Bush, soft-tropical type.
Height: Grows to 24 inches or more, flowers at 6 inches.
Growth: Vigorous, rapid and upright with some spreading.
Branching: Self-branching—facilitated by pinching.
Strength: Soft and succulent, but well able to carry its flowers. Considered sturdy among begonia varieties.

Foliage:
- *Quantity.*—Abundant, each stem having five leaves before a bud is visible.
- *Shape of leaf.*—Ovate with generally crenate margins and palmate ribs and veins.
- *Size of leaf.*—Up to at least 5 inches.
- *Aspect.*—Glossy and smooth.
- *Color.*—Upper side: Waxy; Forest Green; Pl. 23, L–6. Under side: Dull; Grass Green; Pl. 21, L–5. Leaf margin: Upper side; Maroon; Pl. 7, L–7.
- *Leaflets.*—None.
- *Petioles.*—½ to 3 inches long.

THE BUD

Form: Kidney shaped with puffed center.
Size: ¾ to 1 inch when bud is ready to open.
- *Diameter.*—¾ inch.
- *Depth.*—⅜ inch.

Opening: Slowly.
Color: When sepals first divide—Carnival Red; Pl. 3, L–7. Center of opening bud—Oyster White; Pl. 10, B–1.
Sepals: Hooded over bud. Curved downward upon opening and slightly curled back when fully opened.
- *Shape.*—Cup-shaped.
- *Color.*—Inside: Whitish Green; Pl. 17, H–4. Outside: Transparent White; Pl. 17, H–3.

Calyx:
- *Shape.*—Cup-shaped.
- *Size.*—Medium.
- *Aspect.*—Smooth. Calyx splits.

Peduncle:
- *Length.*—2 to 3 inches.
- *Strength.*—Slender; drooping as it develops.
- *Color.*—Light Green.

THE FLOWER

Blooming habit: Continuous and profusely.
Size: Very large, up to 1¼ inches in diameter and 1 inch in depth.
Borne: In a drooping cluster.
Shape: Cup-shaped, with high center and a flat back. Form changes as flower matures and becomes more ball-shaped.
Petalage: Multiple rosettes.
- *Arrangement.*—Imbricated.
- *Color.*—Outer petal: Red; Pl. 2, L–6. Inside petal: Red; Pl. 2, L–6. In some cases, there is a tendency to lighter Rose Red; Pl. 2, G–3. Bottom of petal (hidden part): Rose Red; Pl. 2, C–3. Reverse side: Red; Pl. 2, L–6.

Petaloids: Innumerable, varying from ¼ to ¾ inch in size.
- *Color.*—Bright Red to Light Red depending upon growing temperature in range from 50 to 70°.

Texture: Soft.
Appearance: Glossy.
Discoloration: Only when finished at a high temperature.
Peduncle: 1 to 1½ inches long. Sturdy and upright until flower matures and then it droops.
- *Color.*—Light Green with anthocyanin reddish cast.

Persistence: Flower hangs on and dries under low humidity.
Lasting quality: On plant—up to six weeks. As a cut flower—the same as any double *semperflorens* begonia.
Fragrance: None.
Effect of weather: Hot weather may bleach the color of the flower.

REPRODUCTIVE ORGANS

Stamens: None visible.
Pistils: Very sparse—about ¼ inch long. Flowers are usually sterile.
Stigmas: Almost all flowers are sterile. When found, stigmas are imperfect. Color—Yellow; Pl. 10, E–1.
Ovaries: Typical of *semperflorens* begonia.

My new begonia variety most nearly resembles Swansson Double Pink (unpatented) in its growth habit. The bright red color of the blooms of the new variety, however, are very distinctive and the size of the flower is at least four times larger than any other double red *semperflorens* begonia plant. The new variety is also distinguished by the narrow red colored margin appearing on its leaves, and by its very vigorous growth and huskiness, which surpasses any other commercial variety of double red begonia. The plant, when potted after rooting, will grow to about 6 inches high in about 6 weeks. A fully mature plant in a 6 or 7 inch pot will reach 24 inches in 3 to 4 months, except in the cold dark months of winter when a month or two longer may be required. The colors noted herein were observed on plants grown in a temperature range of 58 to 65° F. at night. When grown at a higher temperature, the flowers will not be as deep in color.

What is claimed is:

1. A new and distinct variety of double *semperflorens* begonia plant substantially as herein shown and described, characterized by its extraordinarily large, bright red flower, by the narrow red colored margin on its leaves, and by its extremely vigorous and husky growth habit.

No references cited.

ROBERT E. BAGWILL, Primary Examiner